United States Patent
Asaumi et al.

(10) Patent No.: US 9,242,948 B2
(45) Date of Patent: Jan. 26, 2016

(54) DIEPOXY COMPOUND, PROCESS FOR PRODUCING SAME, AND COMPOSITION CONTAINING THE DIEPOXY COMPOUND

(75) Inventors: Taku Asaumi, Kobe (JP); Makoto Itagaki, Katano (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 632 days.

(21) Appl. No.: 13/390,705

(22) PCT Filed: Aug. 26, 2010

(86) PCT No.: PCT/JP2010/064979
§ 371 (c)(1),
(2), (4) Date: Feb. 16, 2012

(87) PCT Pub. No.: WO2011/027802
PCT Pub. Date: Mar. 10, 2011

(65) Prior Publication Data
US 2012/0149807 A1  Jun. 14, 2012

(30) Foreign Application Priority Data
Sep. 3, 2009  (JP) ................................ 2009-203536

(51) Int. Cl.
| | |
|---|---|
| C07C 69/88 | (2006.01) |
| C07D 301/27 | (2006.01) |
| C07D 303/12 | (2006.01) |
| C07D 303/32 | (2006.01) |
| C07D 301/28 | (2006.01) |
| C07C 67/08 | (2006.01) |
| C07C 67/31 | (2006.01) |
| C07D 303/22 | (2006.01) |
| C07D 303/28 | (2006.01) |
| C07D 303/30 | (2006.01) |
| C07D 303/40 | (2006.01) |
| C08G 59/22 | (2006.01) |
| C08L 63/00 | (2006.01) |

(52) U.S. Cl.
CPC .............. *C07D 301/28* (2013.01); *C07C 67/08* (2013.01); *C07C 67/31* (2013.01); *C07D 303/22* (2013.01); *C07D 303/28* (2013.01); *C07D 303/30* (2013.01); *C07D 303/40* (2013.01); *C08G 59/22* (2013.01); *C08L 63/00* (2013.01); *C07C 2101/14* (2013.01)

(58) Field of Classification Search
CPC ....................................... C07C 67/08
USPC ........................................................... 528/88
See application file for complete search history.

(56) References Cited

U.S. PATENT DOCUMENTS

| | | | |
|---|---|---|---|
| 4,762,901 A * | 8/1988 | Dhein et al. .................... | 528/73 |
| 5,182,394 A | 1/1993 | Kim | |
| 5,736,620 A * | 4/1998 | Earls et al. ..................... | 525/524 |
| 6,395,351 B1 | 5/2002 | Benecke et al. | |
| 7,538,166 B2 | 5/2009 | Tanaka et al. | |
| 2005/0224753 A1 | 10/2005 | Matayabas et al. | |
| 2007/0184280 A1 | 8/2007 | Tanaka et al. | |
| 2008/0237897 A1 | 10/2008 | Matayabas et al. | |
| 2009/0105388 A1 * | 4/2009 | Tanaka et al. .................. | 524/430 |

FOREIGN PATENT DOCUMENTS

| | | |
|---|---|---|
| JP | 2001-527570 A | 12/2001 |
| JP | 2005-206814 A | 8/2005 |
| WO | 9314078 A1 | 7/1993 |

OTHER PUBLICATIONS

Int'l Search Report issued Sep. 28, 2010 in Int'l Application No. PCT/JP2010/064979.
Mormann et al, "Liquid crystalline thermosets from triaromatic ester group containing diepoxides and aromatic diamines," MAcromolecular Chemistry and Physics, vol. 199, pp. 853-859 (1998).
Ozaki et al, "A Convenient Synthesis of 1-Alkylated 1,4-Benzenediols," Synlett, pp. 365-366 (Apr. 1997).
Int'l Preliminary Report on Patentability issued Apr. 19, 2012 in Int'l Application No. PCT/JP2010/064979.

* cited by examiner

*Primary Examiner* — David Karst
(74) *Attorney, Agent, or Firm* — Panitch Schwarze Belisario & Nadel LLP

(57) ABSTRACT

A diepoxy compound represented by the formula (1)

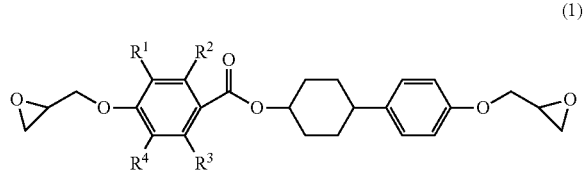

(1)

wherein $R^1$, $R^2$, $R^3$ and $R^4$ independently each represent a hydrogen atom or an alkyl group having 1 to 3 carbon atoms.

18 Claims, No Drawings

DIEPOXY COMPOUND, PROCESS FOR PRODUCING SAME, AND COMPOSITION CONTAINING THE DIEPOXY COMPOUND

CROSS-REFERENCE TO RELATED APPLICATION

This application is a Section 371 of International Application No. PCT/JP2010/064979, filed Aug. 26, 2010, which was published in the Japanese language on Mar. 10, 2011, under International Publication No. WO 2011/027802 A1, and the disclosure of which is incorporated herein by reference.

TECHNICAL FIELD

The present invention relates to a diepoxy compound, a process for producing the same, and a composition containing the diepoxy compound.

BACKGROUND ART

An epoxy cured product obtained by curing a diepoxy compound shows superior properties mechanically and electrically in addition to a good heat resistance and moisture resistance, and is used widely industrially.

In Macromol. Chem. Phys. 199, 853-859 (1998), a diepoxy compound represented by the formula (A)

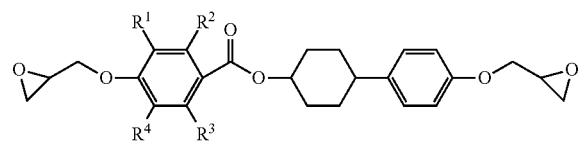

(A)

and a cured product obtained by curing the diepoxy compound and a curing agent are described.

DISCLOSURE OF THE INVENTION

The present invention provides:

[1] A diepoxy compound represented by the formula (1)

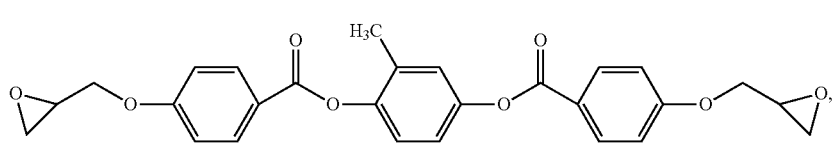

(1)

wherein $R^1$, $R^2$, $R^3$ and $R^4$ independently each represent a hydrogen atom or an alkyl group having 1 to 3 carbon atoms;

[2] The diepoxy compound according to [1], wherein the compound represented by the formula (1) is a compound represented by the formula (1')

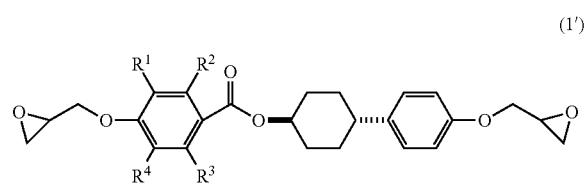

(1')

wherein $R^1$, $R^2$, $R^3$ and $R^4$ are the same meaning as defined above;

[3] A process for producing a diepoxy compound represented by the formula (1)

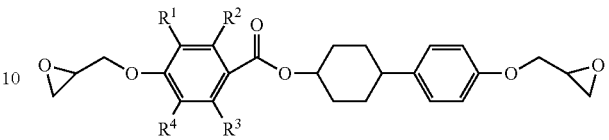

(1)

wherein $R^1$, $R^2$, $R^3$ and $R^4$ independently each represent a hydrogen atom or an alkyl group having 1 to 3 carbon atoms, comprising reacting a dihydroxy compound represented by the formula (2)

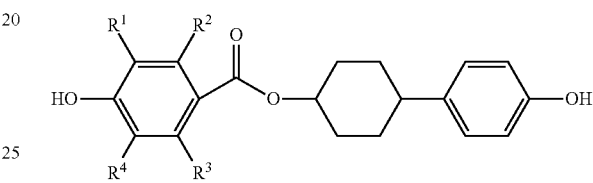

(2)

wherein $R^1$, $R^2$, $R^3$ and $R^4$ are the same meaning as defined above, with an epihalohydrin represented by the formula (3)

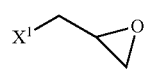

(3)

wherein $X^1$ represents a halogen atom, in the presence of an ammonium salt and an inorganic base;

[4] The process according to [3], wherein the reaction is conducted by mixing the dihydroxy compound represented by the formula (2) with the epihalohydrin represented by the formula (3) and the ammonium salt, and the reaction is further conducted by mixing the mixture obtained with the inorganic base;

[5] The process according to [3] or [4], wherein the inorganic salt is sodium hydroxide or potassium hydroxide;

[6] A dihydroxy compound represented by the formula (2)

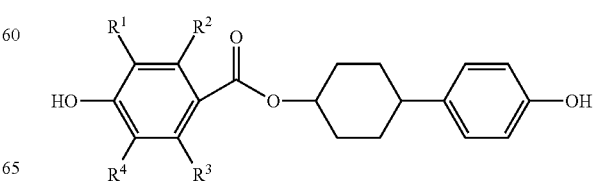

(2)

wherein $R^1$, $R^2$, $R^3$ and $R^4$ independently each represent a hydrogen atom or an alkyl group having 1 to 3 carbon atoms;

[7] The dihydroxy compound according to [6], wherein the compound represented by the formula (2) is a compound represented by the formula (2')

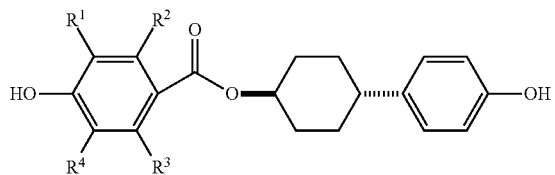

(2')

wherein $R^1$, $R^2$, $R^3$ and $R^4$ independently each represent a hydrogen atom or an alkyl group having 1 to 3 carbon atoms;

[8] A process for producing a dihydroxy compound represented by the formula (2)

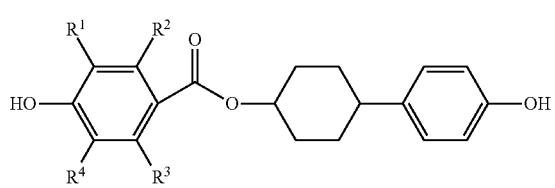

(2)

wherein $R^1$, $R^2$, $R^3$ and $R^4$ independently each represent a hydrogen atom or an alkyl group having 1 to 3 carbon atoms, comprising reacting a compound represented by the formula (5)

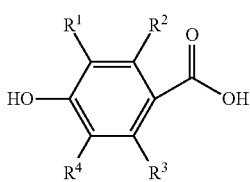

(5)

wherein $R^1$, $R^2$, $R^3$ and $R^4$ are the same meaning as defined above, with a compound represented by the formula (6)

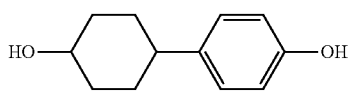

(6)

in the presence of an acid;

[9] A composition containing a diepoxy compound represented by the formula (1)

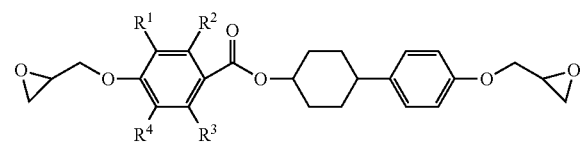

(1)

wherein $R^1$, $R^2$, $R^3$ and $R^4$ independently each represent a hydrogen atom or an alkyl group having 1 to 3 carbon atoms, and a curing agent;

[10] The composition according to [9], wherein the curing agent is at least one curing agent selected from the group consisting of an amine curing agent, a phenol curing agent and an acid anhydride curing agent;

[11] The composition according to [10], wherein the amine curing agent is at least one selected from the group consisting of 4,4'-diaminodiphenylmethane, 4,4'-thaminodiphenylethane, 1,5-diaminonaphthalene and p-phenylenediamine;

[12] A cured product obtained by curing the composition according to any of [9] to [11];

[13] A prepreg obtained by coating on a base material or impregnating a base material with the composition according to any of [9] to [11], followed by semi-curing;

[14] A composition containing a diepoxy compound represented by the formula (1)

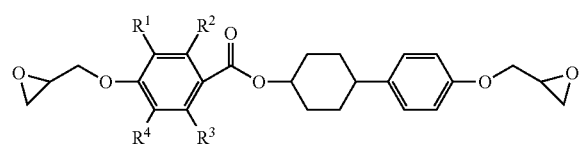

(1)

wherein $R^1$, $R^2$, $R^3$ and $R^4$ independently each represent a hydrogen atom or an alkyl group having 1 to 3 carbon atoms, a curing agent and alumina;

[15] The composition according to [14], which contains 75 to 95 parts by weight of alumina relative to 100 parts by weight of sum of the diepoxy compound represented by the formula (1) and the curing agent;

[16] The composition according to [14] or [15], wherein alumina is a mixture of a component A having D50 (a particle size at 50% cumulative volume) of 2 μm or more and 100 μm or less, a component B having D50 of 1 μm or more and 10 μm or less, and a component C having D50 of 0.01 μm or more and 5 μm or less, and the content of the component A, that of the component B and that of the component C are respectively 50 to 90% by volume, 5 to 40% by volume, and 1 to 30% by volume, relative to 100% by volume of sum of the component A, the component B and the component C;

[17] A cured product obtained by curing the composition according to any of [14] to [16];

[18] The cured product according to [17], wherein the content of alumina contained in the cured product is 50 to 80% by volume.

BEST MODE FOR CARRYING OUT THE PRESENT INVENTION

The diepoxy compound of the present invention is represented by the formula (1)

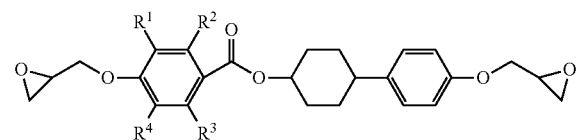

(1)

wherein $R^1$, $R^2$, $R^3$ and $R^4$ independently each represent a hydrogen atom or an alkyl group having 1 to 3 carbon atoms.

Examples of the alkyl group having 1 to 3 carbon atoms include a methyl group, an ethyl group, a propyl group and an isopropyl group, and a methyl group is preferable.

It is preferred that $R^1$, $R^2$, $R^3$ and $R^4$ independently each represent a hydrogen atom or a methyl group, and it is more preferred that $R^1$, $R^2$, $R^3$ and $R^4$ are hydrogen atoms.

As the diepoxy compound represented by the formula (1) (hereinafter, simply referred to as the diepoxy compound (1)), a compound represented by the formula (1')

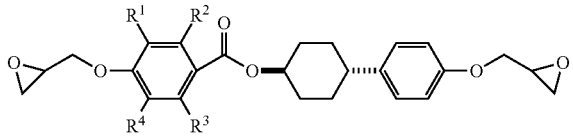

(1')

wherein $R^1$, $R^2$, $R^3$ and $R^4$ are the same meaning as defined above, is preferable.

Examples of the diepoxy compound (1) include 4-{4-(2,3-epoxypropoxy)phenyl}cyclohexyl 4-(2,3-epoxypropoxy) benzoate, 4-{4-(2,3-epoxypropoxy)phenyl}cyclohexyl 4-(2,3-epoxypropoxy)-2-methylbenzoate, 4-{4-(2,3-epoxypropoxy)phenyl}cyclohexyl 4-(2,3-epoxypropoxy)-3-methylbenzoate, 4-{4-(2,3-epoxypropoxy)phenyl}cyclohexyl 4-(2,3-epoxypropoxy)-3-ethylbenzoate, 4-{4-(2,3-epoxypropoxy)phenyl}cyclohexyl 4-(2,3-epoxypropoxy)-2-isopropylbenzoate and 4-{4-(2,3-epoxypropoxy)phenyl}cyclohexyl 4-(2,3-epoxypropoxy)-3,5-dimethylbenzoate, and 4-{4-(2,3-epoxypropoxy)phenyl}cyclohexyl 4-(2,3-epoxypropoxy)benzoate and 4-{4-(2,3-epoxypropoxy)phenyl}cyclohexyl 4-(2,3-epoxypropoxy)-3-methylbenzoate are preferable.

The diepoxy compound (1) can be produced by reacting a dihydroxy compound represented by the formula (2)

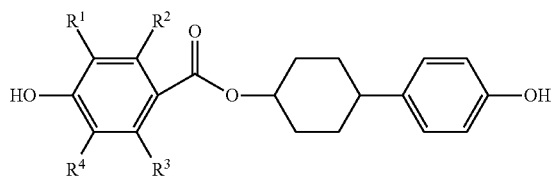

(2)

wherein $R^1$, $R^2$, $R^3$ and $R^4$ are the same meaning as defined above (hereinafter, simply referred to as the compound (2)), with an epihalohydrin represented by the formula (3)

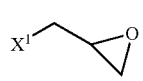

(3)

wherein $X^1$ represents a halogen atom (hereinafter, simply referred to as the epihalohydrin (3)), in the presence of an ammonium salt and an inorganic base.

As the compound (2), a compound represented by the formula (2')

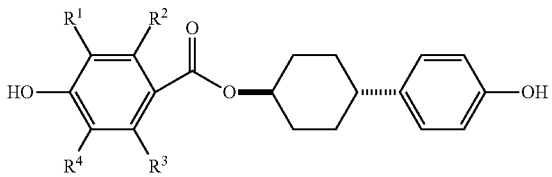

(2')

wherein $R^1$, $R^2$, $R^3$ and $R^4$ are the same meaning as defined above, is preferable. The compound represented by the formula (1') can be obtained by using the compound represented by the formula (2').

Examples of the compound (2) include 4-(4-hydroxyphenyl)cyclohexyl 4-hydroxybenzoate, 4-(hydroxyphenyl)cyclohexyl 4-hydroxy-2-methylbenzoate, 4-(hydroxylphenyl)cyclohexyl 4-hydroxy-3-methylbenzoate, 4-(hydroxylphenyl)cyclohexyl 4-hydroxy-3-ethylbenzoate, 4-(hydroxylphenyl)cyclohexyl 4-hydroxy-2-propylbenzoate and 4-(hydroxyphenyl)cyclohexyl 4-hydroxy-3,5-dimethylbenzoate.

$X^1$ in the epihalohydrin (3) represents a halogen atom, and examples of the halogen atom include a chlorine atom and a bromine atom, and a chlorine atom is preferable.

Examples of the epihalohydrin (3) include epichlorohydrin and epibromohydrin, and epichlorohydrin is preferable. Two or more kinds of the epihalohydrin may be used in combination.

The amount to be used of the epihalohydrin (3) is usually 2 to 200 moles relative to 1 mole of the compound (2), and preferably 5 to 150 moles.

Examples of the ammonium salt include a quaternary ammonium halide such as tetramethylammonium chloride, tetraethylammonium chloride, tetrabutylammonium chloride, benzyltrimethylammonium chloride, benzyltriethylammonium chloride, benzyltributylammonium chloride, tetramethylammonium bromide, tetraethylammonium bromide, tetrabutylammonium bromide, benzyltrimethylammonium bromide, benzyltriethylammonium bromide, tetramethylammonium iodide, tetraethylammonium iodide, tetrabutylammonium iodide and benzyltributylammonium iodide, and a quaternary ammonium bromide is preferable, and tetrabutylammonium bromide and benzyltrimethylammonium bromide are more preferable.

Two or more kinds of the ammonium salts may be used in combination.

The amount to be used of the ammonium salt is usually 0.0001 to 1 mole relative to 1 mole of the compound (2), and preferably 0.001 to 0.5 mole.

Examples of the inorganic base include an alkali metal hydroxide such as lithium hydroxide, sodium hydroxide and potassium hydroxide, and an alkali metal carbonate such as sodium carbonate and potassium carbonate, and an alkali metal hydroxide is preferable, and sodium hydroxide and potassium hydroxide are more preferable.

Two or more kinds of the inorganic bases may be used in combination.

The amount to be used of the inorganic base is usually 0.1 to 20 moles relative to 1 mole of the compound (2), and preferably 0.5 to 10 moles.

The inorganic base in a solid form such as granular one may be used, and the inorganic base in an aqueous solution form having about 1 to about 60% by weight concentration may be used.

The reaction of the compound (2) and the epihalohydrin (3) may be carried out in the absence of a solvent and may be conducted in the presence of a solvent.

Examples of the solvent include an alcohol solvent such as methanol, ethanol, propanol, butanol, ethylene glycol, propylene glycol, 2-butanol, 2-pentanol, 3-pentanol, 2-hexanol, 3-hexanol, 2-heptanol, 3-heptanol, 2-octanol, 4-decanol, 2-dodecanol, 3-methyl-2-butanol, 3,3-dimethyl-2-butanol, 3-methyl-2-pentanol, 5-methyl-2-hexanol, 4-methyl-3-heptanol, 2-methyl-2-propanol, 2-methyl-2-butanol, 2,3-dimethyl-2-butanol, 2-methyl-2-pentnaol, 3-methyl-3-pentanol, 3-ethyl-3-pentnaol, 2,3-dimethyl-3-pentanol, 3-ethyl-2,2-dimethyl-3-pentanol, 2-methyl-2-hexanol and 3,7-dimethyl-3-octanol, a ketone solvent such as methyl ethyl ketone and methyl isobutyl ketone, an aprotic polar solvent such as N,N-dimethylformamide, N,N-dimethylacetamide and N-methylpyrrolidone, acetonitrile, benzonitrile and dimethylsulfoxide, and an ether solvent such as diethyl ether, tert-butyl methyl ether, 1,2-dimethoxyethane, 1,4-dioxane, tetrahydrofuran and anisole. Two or more kinds of the solvents may be used in combination.

When the reaction carried out in the presence of the solvent, the amount to be used thereof is usually 0.01 to 100 parts by weight relative to 1 part by weight of the compound (2), and preferably 0.1 to 50 parts by weight.

The reaction may be conducted under a normal pressure condition, or may be conducted under a pressurized condition, or may be conducted under a reduced pressure condition. Alternatively, the reaction may be carried out under an atmosphere of an inert gas such as nitrogen gas and argon gas.

The reaction is usually conducted by mixing the compound (2), the epihalohydrin (3), the ammonium salt, the inorganic base and if necessary, the solvent. While the order of mixing them is not limited, it is preferred that the reaction is conducted by mixing the compound (2) with the epihalohydrin (3) and the ammonium salt, and the reaction is further conducted by mixing the mixture obtained with the inorganic base.

The reaction temperature is usually −20° C. to 150° C., and preferably −10° C. to 120° C.

The reaction time is usually 1 to 150 hours.

When the reaction is conducted by mixing the compound (2) with the epihalohydrin (3) and the ammonium salt, and the reaction is further conducted by mixing the mixture obtained with the inorganic base, the temperature wherein the compound (2), the epihalohydrin (3) and the ammonium salt are mixed is preferably −10° C. to 150° C., and more preferably 0° C. to 120° C. The temperature wherein the mixture obtained is mixed with the inorganic base is preferably −20° C. to 120° C., and more preferably −10° C. to 80° C.

The progress of the reaction can be checked by a conventional analytical means such as liquid chromatography.

After completion of the reaction, an organic layer containing the diepoxy compound (1) is obtained, for example, by mixing the reaction mixture, water and if necessary, a water-insoluble solvent, conducting stirring and then, conducting separation. The diepoxy compound (1) can be isolated, for example, by washing the organic layer obtained with water, if necessary, removing an insoluble matter by filtration, and then, conducting concentration.

The diepoxy compound (1) isolated can be further purified with a conventional purification means such as recrystallization.

The diepoxy compound (1) can be also produced by reacting the compound (2) with a compound represented by the formula (4)

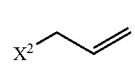

(4)

wherein $X^2$ represents a halogen atom (hereinafter, simply referred to as the compound (4)), in the presence of a base to obtain a compound represented by the formula (7)

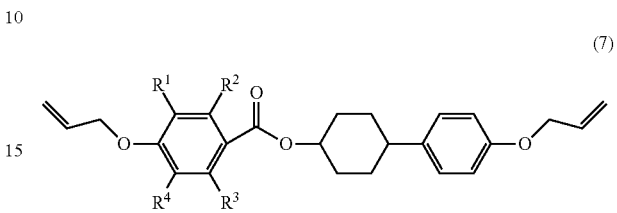

(7)

wherein $R^1$, $R^2$, $R^3$ and $R^4$ are the same meaning as defined above (hereinafter, simply referred to as the compound (7)), and then oxidizing the compound (7) obtained with an oxidizing agent.

$X^2$ in the compound (4) represents a halogen atom, and examples of the halogen atom include a chlorine atom and a bromine atom.

Examples of the compound (4) include allyl chloride and allyl bromide.

Two or more kinds of the compound (4) may be used in combination.

The amount to be used of the compound (4) is usually 2 to 200 moles relative to 1 mole of the compound (2), and preferably 2 to 100 moles.

The base may be an inorganic base and may be an organic base, and an inorganic base is preferable. Examples of the inorganic base include an alkali metal hydroxide such as lithium hydroxide, sodium hydroxide and potassium hydroxide, and an alkali metal carbonate such as sodium carbonate and potassium carbonate. Examples of the organic base include pyridine. Among them, preferred is an alkali metal carbonate, and more preferred are sodium carbonate and potassium carbonate.

Two or more kinds of the bases may be used in combination.

The amount to be used of the base is usually 2 to 10 moles relative to 1 mole of the compound (2). When the organic base which is liquid under the reaction condition is used, excess amount of the organic base may be used also to serve as the solvent.

While the reaction of the compound (2) and the compound (4) may be conducted in the absence of a solvent, it is preferably carried out in the presence of a solvent. Examples of the solvent include the same as those used in the above-mentioned reaction of the compound (2) with the epihalohydrine (3). Alternatively, when the organic base which is liquid under the reaction condition is used, the organic base may be used as the solvent, as described above.

The reaction of the compound (2) and the compound (4) is usually conducted by mixing the compound (2), the compound (4), the base and if necessary, the solvent, and the mixing order thereof is not limited. The reaction may be carried out under a normal pressure condition, under a pressurized condition or under a reduced pressure condition. Alternatively, the reaction may be conducted under an atmosphere of an inert gas such as nitrogen gas and argon gas. The reaction temperature is usually −20° C. to 120° C., and preferably −10° C. to 100° C. The progress of the reaction can be checked by a conventional analytical means such as liquid chromatography, and the reaction is preferably conducted until the increase of the producing amount of the compound (7) do not become recognized.

The obtained reaction mixture containing the compound (7) is usually mixed with an oxidizing agent as it is or after washing with water to conduct the reaction of the compound (7) and the oxidizing agent.

The oxidizing agent may be an oxidizing agent capable of converting a carbon-carbon double bond to an epoxy group, and specific examples thereof include a peracid such as m-chloroperbenzoic acid. The amount to be used of the oxidizing agent is usually 2 to 20 moles relative to 1 mole of the compound (7).

The reaction of the compound (7) and the oxidizing agent may be carried out under a normal pressure condition, under a pressurized condition or under a reduced pressure condition. Alternatively, the reaction may be conducted under an atmosphere of an inert gas such as nitrogen gas and argon gas. The reaction temperature is usually −20° C. to 120° C., and preferably −10° C. to 100° C. The reaction time is usually 0.5 to 72 hours. The progress of the reaction can be checked by a conventional analytical means such as liquid chromatography.

After completion of the reaction, the diepoxy compound (1) can be isolated, for example, by concentrating the reaction mixture. The concentration may be carried out after decomposing the oxidizing agent remaining in the reaction mixture. The diepoxy compound (1) isolated can be further purified with a conventional purification means such as recrystallization.

The compound (2) can be produced, for example, by reacting a compound represented by the formula (5)

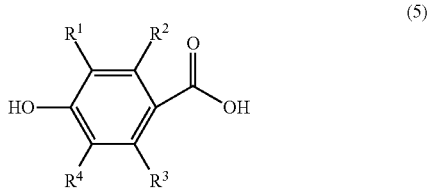

(5)

$R^1$, $R^2$, $R^3$ and $R^4$ independently each represent a hydrogen atom or an alkyl group having 1 to 3 carbon atoms (hereinafter, simply referred to as the compound (5)), with a compound represented by the formula (6)

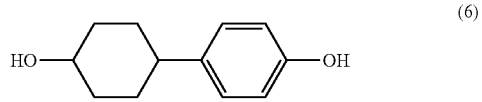 [SMILES: Oc1ccc(C2CCC(O)CC2)cc1]

(6)

(hereinafter, simply referred to as the compound (6)) in the presence of an acid.

Examples of the compound (5) include 4-hydroxybenzoic acid, 4-hydroxy-2-methylbenzoic acid, 4-hydroxy-3-methylbenzoic acid, 4-hydroxy-2-ethylbenzoic acid, 4-hydroxy-3-ethylbenzoic acid, 4-hydroxy-2-isopropylbenzoic acid, 4-hydroxy-3-propylbenzoic acid and 4-hydroxy-3,5-dimethylbenzoic acid, and 4-hydroxybenzoic acid and 4-hydroxy-3-methylbenzoic acid are preferable.

As the compound (6), a compound represented by the formula (6')

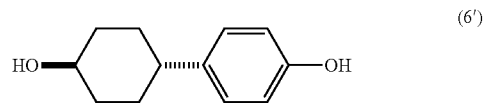

(6')

is preferable.

As the compound (6), a commercially available one is usually used. Alternatively, the compound represented by the formula (6') can be also produced according to the process described in JP Patent No. 3930669.

The amount to be used of the compound (6) is usually 1 to 30 moles relative to 1 mole of the compound (5), and preferably 1 to 15 moles.

Examples of the acid include sulfuric acid and p-toluenesulfonic acid. Two or more kinds of the acids may be used in combination. The amount to be used of the acid is usually 0.001 to 0.3 mole relative to 1 mole of the compound (5).

The reaction of the compound (5) and the compound (6) is preferably carried out in the presence of a solvent. Examples of the solvent include an aliphatic hydrocarbon solvent such as hexane, heptane and octane, and an aromatic hydrocarbon solvent such as benzene, toluene, ethylbenzene, xylene, mesitylene, chlorobenzene and dichlorobenzene. The amount to be used of the solvent is usually 1 to 200 parts by weight relative to 1 part by weight of the compound (5), and preferably 5 to 100 parts by weight.

The reaction of the compound (5) and the compound (6) may be carried out under a normal pressure condition, under a pressurized condition or under a reduced pressure condition. Alternatively, the reaction may be conducted under an atmosphere of an inert gas such as nitrogen gas and argon gas. The reaction temperature is usually 50 to 250° C., and preferably 60 to 200° C. While the reaction time differs depending on the reaction temperature, it is usually 0.5 to 72 hours. Water is generated with the progress of the reaction, and the reaction is preferably performed while removing water generated out of the reaction system. Examples of the method of removing water generated out of the reaction system include an azeotropic distillation method and a method using a dehydrating agent such as molecular sieves.

Next, the composition containing the diepoxy compound (1) and a curing agent (hereinafter, simply referred to as the composition X) will be illustrated.

The composition X can contain two or more kinds of the diepoxy compound (1). Alternatively, the composition X can contain two or more kinds of the curing agent.

The composition X can contain a solvent in addition to the diepoxy compound (1) and the curing agent. The composition X preferably contains a solvent from the viewpoint of its easy preparation. Examples of the solvent include a ketone solvent such as methyl ethyl ketone and methyl isobutyl ketone, an aprotic polar solvent such as dimethylsulfoxide and N-methylpyrrolidone, an ester solvent such as butyl acetate and a glycol solvent such as propylene glycol monomethyl ether. A ketone solvent is preferable, and methyl isobutyl ketone is more preferable. The diepoxy compound (1) has superior solubility in methyl isobutyl ketone, and therefore, it has a tendency for having superior solubility in the above-mentioned solvent.

The curing agent may be one having at least one functional group capable of causing a curing reaction with an epoxy group in the diepoxy compound (1) or one showing a catalytic activity in the curing reaction of the epoxy compound (1). Specific examples thereof include an amine curing agent wherein the above-mentioned functional group is an amino group, a phenol curing agent wherein the above-mentioned functional group is a hydroxyl group, an acid anhydride curing agent wherein the above-mentioned functional group is a group represented by —CO—O—CO— and a curing catalyst, and an amine curing agent, a phenol curing agent and a curing catalyst are preferable.

Examples of the amine curing agent include an aliphatic polyvalent amine having 2 to 20 carbon atoms such as ethylenediamine, trimethylenediamine, tetramethylenediamine, hexamethylenediamine, diethylenetriamine and triethylenetetramine, an aromatic polyvalent amine such as p-xylenediamine, m-xylenediamine, 1,5-diaminonaphthalene, m-phenylenediamine, p-phenylenediamine, 4,4'-diaminodiphenylmethane, 4,4'-diaminodiphenylethane, 4,4'-diaminodiphenylpropane, 4,4'-diaminodiphenyl ether, 1,1-bis(4-aminophenyl)cyclohexane, 4,4'-diaminodiphenylsulfone and bis(4-aminophenyl)phenylmethane, an alicyclic polyvalent amine such as 4,4'-diaminodicyclohexane and 1,3-bis(aminomethyl)cyclohexane, and dicyandiamide. Among them, preferred are an aromatic polyvalent amine and dicyandiamide, and more preferred are 4,4'-diaminodiphenylmethane, 4,4'-diaminodiphenylethane, 1,5-diaminonaphthalene, p-phenylenediamine and dicyandiamide.

Examples of the phenol curing agent include a phenol resin, a phenol aralkyl resin (having a phenylene skeleton, a diphenylene skeleton or the like), a naphthol aralkyl resin and a polyoxystyrene resin. Examples of the phenol resin include a resol type phenol resin such as an aniline-modified resol resin and a dimethyl ether resol resin, a novolak type phenol resin such as a phenol novolak resin, a cresol novolak resin, a tert-butylphenol novolak resin and a nonylphenol novolak resin, a special phenol resin such as a dicyclopentadiene-modified phenol resin, a terpene-modified phenol resin and a triphenol methane type resin. Examples of the polyoxystyrene resin include poly(p-oxystyrene).

Examples of the acid anhydride curing agent include maleic anhydride, phthalic anhydride, pyromellitic anhydride, trimellitic anhydride, cis-4-cyclohexene-1,2-dicarboxylic anhydride and 5-(2,5-dioxotetrahydrofuryl)-3-methyl-3-cyclohexene-1,2-dicarboxylic anhydride.

Examples of the curing catalyst include 2-methylimidazole, 2-ethyl-4-methylimidazole, 2-heptadecylimidazole and benzyldimethylamine.

The amount to be used of the curing agent may be suitably selected depending on its kind. When the amine curing agent or the phenol curing agent is used, it is used in the amount wherein the total amount of functional groups capable of causing a curing reaction with an epoxy group in the curing agent becomes 0.5 to 1.5 moles relative to 1 mole of the epoxy group in the diepoxy compound (1), and preferably 0.9 to 1.1 moles.

The composition X can contain, in addition to the diepoxy compound (1), the curing agent and the solvent, another compound having an epoxy group or various additives as long as desired performances of the cured product obtained by curing the composition X are not decreased.

Examples of another compound having an epoxy group include bisphenol A type epoxy compound, ortho-cresol type epoxy compound, biphenol diglycidyl ether, 4,4'-bis(3,4-epoxybuten-1-yloxy)phenyl benzoate, naphthalene diglycidyl ether and α-methylstilbene-4,4'-diglycidyl ether.

Examples of the additive include a curing accelerator such as triphenylphosphine, 1,8-azabicyclo[5.4.0]-7-undecene and 2-phenylimidazole; a coupling agent such as γ-glycidoxypropyltrimethoxysilane; a colorant such as carbon black; a low-stress component such as silicone oil and silicone rubber; a mold release agent such as natural wax, synthetic wax, higher fatty acid or metal salt thereof, and paraffin; an antioxidant; silica such as fused crushed silica powder, fused spherical silica powder, crystal silica powder and secondary cohesive silica powder; alumina such as α-alumina or transition alumina (γ-alumina, θ-alumina, δ-alumina); titanium white; aluminum hydroxide; talc; clay; mica; and glass fiber.

The composition X preferably contains alumina from the viewpoint of improving the thermal conductivity of the cured product obtained by curing the composition X. As the composition X, a composition containing the diepoxy compound (1), the curing agent and alumina is preferable, and the composition X preferably contains the above-mentioned solvent from the viewpoint of preparing it easily.

When the composition X contains alumina, the content of alumina is usually 75 parts by weight to 95 parts by weight relative to 100 parts by weight of sum of the diepoxy compound (1) and the curing agent. The composition containing alumina of which amount is 75 parts by weight or more relative to 100 parts by weight of sum of the diepoxy compound (1) and the curing agent tends to improve the thermal conductivity of the cured product obtained by curing the composition, and the composition wherein the amount of alumina is 95 parts by weight or less tends to be molded easily.

As alumina, powdery alumina is preferable, and alumina powder which is a mixture of the component A having D50 of 2 μm or more and 100 μm or less, the component B having D50 of 1 μm or more and 10 μm or less, and the component C having D50 of 0.01 μm or more and 5 μm or less, in which D50 is a particle size at 50% cumulative volume from the smallest particle side of a weight cumulative particle size distribution (average particle size), is more preferable. Alternatively, the content of the component A, that of the component B and that of the component C are respectively 50 to 90% by volume, 5 to 40% by volume, and 1 to 30% by volume, relative to 100% by volume of sum of the component A, the component B and the component C is preferable. Such alumina can be prepared by appropriately mixing commercially available alumina powder having various average particle sizes.

Alternatively, the content of alumina contained in the cured product is preferably 50 to 80% by volume relative to 100% by volume of the cured product.

Examples of the method of producing the cured product obtained by curing the composition X include a method of curing the composition X as it is by heating to a predetermined temperature, a method of melting the composition X with heating, injecting it into a mold, further heating the mold and molding, a method of melting the composition X, injecting the resultant melting product in a mold previously heated and curing it, a method of partially curing the composition X, grinding the partially cured product obtained, filling a mold with the powder obtained and melt-molding the filled powder, and a method of dissolving the composition X in a solvent, as necessary, partially curing it with stirring, casting the resultant solution, drying and removing the solvent through ventilation drying or the like, and heating for a predetermined time, if necessary, while applying a pressure using a press or the like.

Also, a prepreg can also be produced by, if necessary, diluting the composition X with a solvent, coating on a base material or impregnating a base material with composition X, and heating the base material obtained to semi-cure the diepoxy compound (1) in the base material. Laminate plates can be obtained by laminating plural prepregs and pressurizing and heating it by press or the like.

Examples of the base material used for prepreg include woven or nonwoven fabric of an inorganic fiber such as glass fiber and carbon fiber, and woven or nonwoven fabric of an organic fiber such as polyester fiber.

The cured product obtained by curing the composition X has a superior thermal conductivity, and the cured product obtained by curing the composition X containing alumina has more superior thermal conductivity.

EXAMPLES

The present invention will be illustrated specifically by Examples and Comparative Examples below, but the present invention is not limited to these Examples.

Example 1

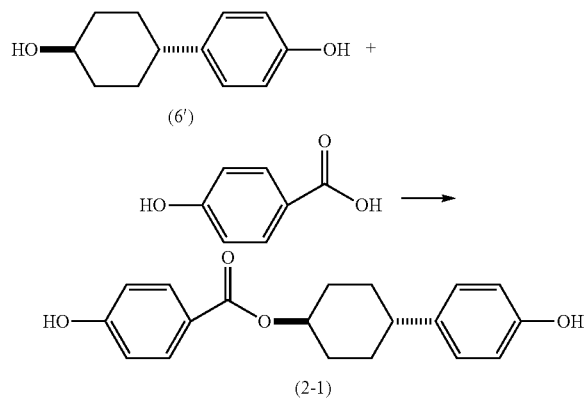

To a reaction container equipped with a Dean-Stark apparatus, 11.0 g of 4-hydroxybenzoic acid, 19.9 g of the compound represented by the above-mentioned formula (6'), 1.51 g of p-toluenesulfonic acid and 220 g of chlorobenzene were added at room temperature (about 25° C.). The mixture obtained was stirred for 16 hours under reflux thereby conducting a reaction. Water generated with the progress of the reaction was removed continuously out of the reaction system using a Dean-Stark apparatus. After completion of the reaction, the reaction mixture was cooled down to room temperature. The solid precipitated was isolated by filtration to obtain a crude product.

To a reaction container equipped with a cooling apparatus, the crude product obtained, 700 mL of chloroform and 100 mL of ethanol were added, and the mixture obtained was stirred at 55° C. for 1 hour. The mixture obtained was cooled down to room temperature, and further kept at 5° C. over night. Then, the solid precipitated was isolated by filtration and washed with 45 mL of chloroform, and then, dried at 50° C. for 4 hours under reduced pressure to obtain 11.67 g of pale gray color crystals of the compound represented by the above-mentioned formula (2-1).

The crystals obtained were analyzed with a liquid chromatography, and the area percentage of the peak of the compound represented by the formula (2-1) in the chromatograph was 96.7%. If the content of the compound represented by the formula (2-1) in the crystals was 96.7% by weight, the yield of the compound represented by the formula (2-1) based on 4-hydroxybenzoic acid was 45%.

$^1$H-NMR spectrum data (δ: ppm, dimethylsulfoxide-$d_6$) 10.30 (s, 1H), 9.13 (s, 1H), 7.82 (d, 2H), 7.05 (d, 2H), 6.85 (d, 2H), 6.68 (d, 2H), 4.87 (m, 1H), 1.28-2.62 (c, 9H)

Example 2

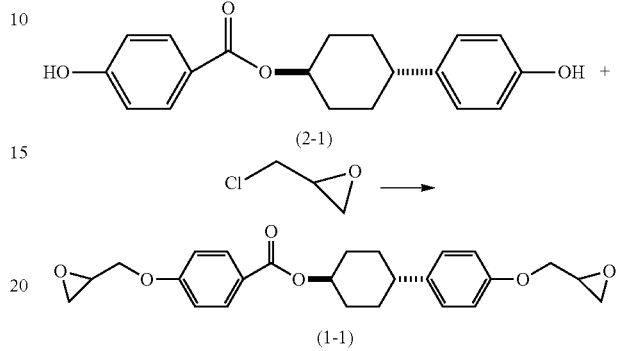

To a reaction container equipped with a cooling apparatus, 11.0 g of the crystals of the compound represented by the formula (2-1) which was obtained in the above-mentioned Example 1, 1.70 g of tetrabutylammonium bromide, 130 g of epichlorohydrin and 85.9 g of 2-methyl-2-propanol were added at room temperature. The mixture obtained was stirred at 70° C. for 22 hours, and then, cooled down to 18° C. To the mixture obtained, 28.2 g of 15% by weight aqueous sodium hydroxide solution was gradually added. The mixture obtained was stirred at 18° C. for 2 hours, and then, cooled down to 0° C.

To the reaction mixture obtained, 275 mL of ion-exchanged water was added, and 825 mL of chloroform was added thereto at room temperature. The mixture obtained was stirred, and then, separated into a chloroform layer and an aqueous layer. The chloroform layer was washed three times with ion-exchanged water, and then, an insoluble matter was removed by filtration. The filtrate obtained was concentrated to obtain a crude product.

To a reaction container equipped with a cooling apparatus, the crude product obtained, 143 mL of toluene and 220 mL of 2-propanol were added, and the mixture obtained was stirred at 70° C. for 3 hours. The mixture obtained was cooled down to room temperature, and further kept at 5° C. over night. Then, the solid precipitated was isolated by filtration. The solid isolated was washed with 2-propanol, and then, dried to obtain 12.51 g of white crystals of the compound represented by the above-mentioned formula (1-1).

The crystals obtained were analyzed with a liquid chromatography, and the area percentage of the peak of the compound represented by the formula (1-1) in the chromatograph was 93.7%. If the content of the compound represented by the formula (1-1) in the crystals was 93.7% by weight, the yield of the compound represented by the formula (1-1) based on the compound represented by the formula (2-1) was 81%.

$^1$H-NMR spectrum data (δ: ppm, $CDCl_3$) 8.01 (d, 2H), 7.14 (d, 2H), 6.95 (d, 2H), 6.87 (d, 2H), 4.99 (m, 1H), 4.31 (dd, 1H), 4.20 (dd, 1H), 3.88-4.08 (c, 2H), 3.30-3.45 (c, 2H), 2.84-3.00 (c, 2H), 2.70-2.80 (c, 2H), 2.53 (m, 1H), 2.10-2.32 (c, 2H), 1.85-2.09 (c, 2H), 1.50-1.80 (c, 4H)

Example 3

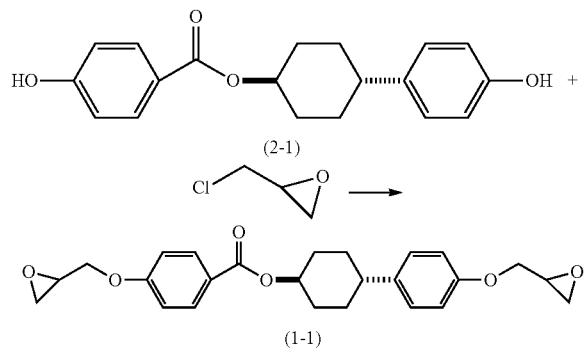

The compound represented by the formula (2-1) was prepared according to the process described in Example 1. It was assumed that the content of the compound represented by the formula (2-1) which was obtained was 96.6% by weight based on the area percentage of the peak of the compound represented by the formula (2-1) in the chromatograph obtained by a liquid chromatography analysis.

To a reaction container equipped with a cooling apparatus, 2.0 g of the compound represented by the formula (2-1) which was prepared in the above, 0.62 g of tetrabutylammonium bromide and 23.7 g of epichlorohydrin were added at room temperature. The mixture obtained was stirred at 70° C. for 5 hours, and then, cooled down to 18° C. To the mixture obtained, 5.12 g of 15% by weight aqueous sodium hydroxide solution was gradually added. The mixture obtained was stirred at 18° C. for 2 hours, and then, cooled down to 0° C.

To the reaction mixture obtained, 50 mL of ion-exchanged water was added, and 150 mL of chloroform was added thereto at room temperature. The mixture obtained was stirred, and then, separated into a chloroform layer and an aqueous layer. The chloroform layer was washed three times with ion-exchanged water, and then, an insoluble matter was removed by filtration. The filtrate obtained was concentrated to obtain a crude product.

To a reaction container equipped with a cooling apparatus, the crude product obtained, 25 mL of toluene and 39 mL of 2-propanol were added, and the mixture obtained was stirred at 70° C. for 1 hour. The mixture obtained was cooled down to room temperature, and further kept at 5° C. over night. Then, the solid precipitated was isolated by filtration. The solid isolated was washed with 2-propanol, and then, dried to obtain 2.32 g of white crystals of the compound represented by the above-mentioned formula (1-1).

The crystals obtained were analyzed with a liquid chromatography, and the area percentage of the peak of the compound represented by the formula (1-1) in the chromatograph was 95.0%. If the content of the compound represented by the formula (1-1) in the crystals was 95.0% by weight, the yield of the compound represented by the formula (1-1) based on the compound represented by the formula (2-1) was 84%.

Example 4

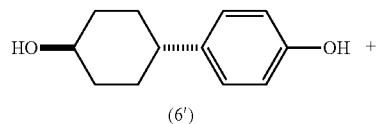

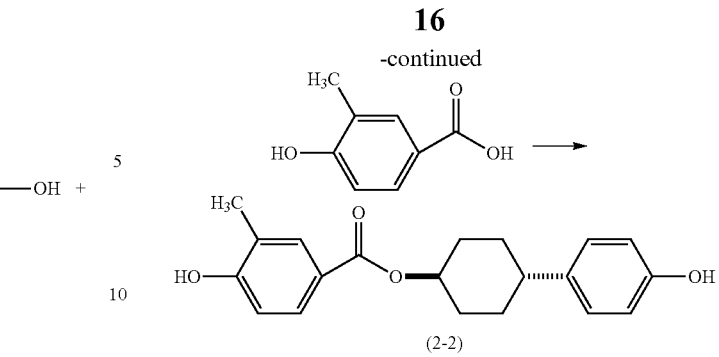

To a reaction container equipped with a Dean-Stark apparatus, 6.00 g of 4-hydroxy-3-methylbenzoic acid, 9.10 g of the compound represented by the above-mentioned formula (6'), 0.75 g of p-toluenesulfonic acid and 85 g of xylene were added at room temperature (about 25° C.). The mixture obtained was stirred for 2.5 hours under reflux thereby conducting a reaction. Water generated with the progress of the reaction was removed continuously out of the reaction system using a Dean-Stark apparatus. After completion of the reaction, the reaction mixture was cooled down to room temperature. The solid precipitated was isolated by filtration to obtain a crude product. The crude product obtained was washed with 200 mL of methanol, and then, dried at 50° C. for 4 hours under reduced pressure to obtain 2.01 g of pale gray color crystals of the compound represented by the above-mentioned formula (2-2).

The crystals obtained were analyzed with a liquid chromatography, and the area percentage of the peak of the compound represented by the formula (2-2) in the chromatograph was 89.6%. If the content of the compound represented by the formula (2-2) in the crystals was 89.6% by weight, the yield of the compound represented by the formula (2-2) based on 4-hydroxy-3-methylbenzoic acid was 14%.

$^1$H-NMR spectrum data (δ: ppm, dimethylsulfoxide-$d_6$) 10.24 (s, 1H), 9.15 (s, 1H), 7.66 (m, 2H), 7.02 (d, 2H), 6.85 (d, 1H), 6.67 (d, 2H), 4.84 (m, 1H), 1.18-2.66 (c, 12H)

Example 5

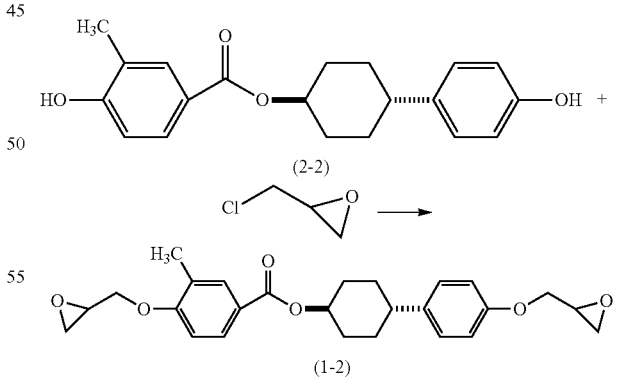

To a reaction container equipped with a cooling apparatus, 0.75 g of the crystals of the compound represented by the formula (2-2) which was obtained in the above-mentioned Example 4, 0.22 g of tetrabutylammonium bromide, 8.50 g of epichlorohydrin and 5.61 g of 2-methyl-2-propanol were added at room temperature. The mixture obtained was stirred at 70° C. for 15 hours, and then, cooled down to 18° C. To the mixture obtained, 1.84 g of 15% by weight aqueous sodium hydroxide solution was gradually added. The mixture obtained was stirred at 18° C. for 6 hours, and then, cooled down to 0° C.

To the reaction mixture obtained, 25 mL of ion-exchanged water was added, and 75 mL of chloroform was added thereto at room temperature. The mixture obtained was stirred, and then, separated into a chloroform layer and an aqueous layer. The chloroform layer was washed three times with ion-exchanged water, and then, an insoluble matter was removed by filtration. The filtrate obtained was concentrated to obtain a crude product.

To a reaction container equipped with a cooling apparatus, the crude product obtained, 10 mL of toluene and 15 mL of 2-propanol were added, and the mixture obtained was stirred at 70° C. for 1 hour. The mixture obtained was cooled down to room temperature, and then, the solid precipitated was isolated by filtration. The solid isolated was washed with 2-propanol, and then, dried to obtain 0.58 g of white crystals of the compound represented by the above-mentioned formula (1-2).

The crystals obtained were analyzed with a liquid chromatography, and the area percentage of the peak of the compound represented by the formula (1-2) in the chromatograph was 94.6%. If the content of the compound represented by the formula (1-2) in the crystals was 94.6% by weight, the yield of the compound represented by the formula (1-2) based on the compound represented by the formula (2-2) was 61%.

$^1$H-NMR spectrum data (δ: ppm, CDCl$_3$) 7.88 (m, 2H), 7.15 (d, 2H), 6.75-7.00 (c, 3H), 4.99 (m, 1H), 4.32 (dd, 1H), 4.20 (dd, 1H), 3.90-4.08 (c, 2H), 3.30-3.47 (c, 2H), 2.86-3.00 (c, 2H), 2.71-2.85 (c, 2H), 2.53 (m, 1H), 2.12-2.37 (c, 5H), 1.87-2.09 (c, 2H), 1.51-1.78 (c, 4H)

Example 6

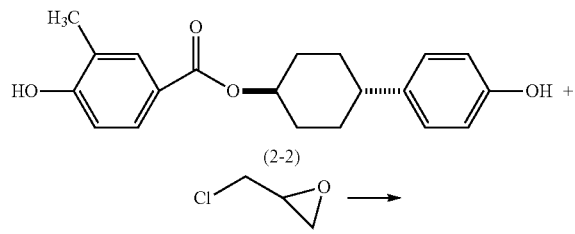

-continued

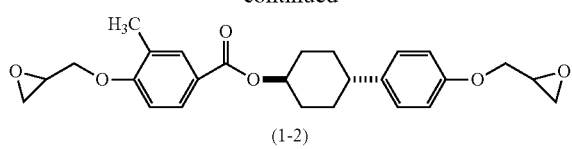

The compound represented by the formula (2-2) was prepared according to the process described in Example 4. It was assumed that the content of the compound represented by the formula (2-2) which was obtained was 94.9% by weight based on the area percentage of the peak of the compound represented by the formula (2-2) in the chromatograph obtained by a liquid chromatography analysis.

To a reaction container equipped with a cooling apparatus, 26.0 g of the compound represented by the formula (2-2) which was prepared in the above, 7.70 g of tetrabutylammonium bromide and 290 g of epichlorohydrin were added at room temperature. The mixture obtained was stirred at 70° C. for 6 hours, and then, cooled down to 18° C. To the mixture obtained, 63.7 g of 15% by weight aqueous sodium hydroxide solution was gradually added. The mixture obtained was stirred at 18° C. for 2 hours, and then, cooled down to 0° C.

To the reaction mixture obtained, 900 mL of ion-exchanged water was added, and 195 mL of chloroform was added thereto at room temperature. The mixture obtained was stirred, and then, separated into a chloroform layer and an aqueous layer. The chloroform layer was washed three times with ion-exchanged water, and then, an insoluble matter was removed by filtration. The filtrate obtained was concentrated to obtain a crude product.

To a reaction container equipped with a cooling apparatus, the crude product obtained, 252 mL of toluene and 419 mL of 2-propanol were added, and the mixture obtained was stirred at 70° C. for 1 hour. The mixture obtained was cooled down to room temperature, and further kept at 5° C. over night. Then, the solid precipitated was isolated by filtration. The solid isolated was washed with 2-propanol, and then, dried to obtain 30.14 g of white crystals of the compound represented by the above-mentioned formula (1-2).

The crystals obtained were analyzed with a liquid chromatography, and the area percentage of the peak of the compound represented by the formula (1-2) in the chromatograph was 95.0%. If the content of the compound represented by the formula (1-2) in the crystals was 95.0% by weight, the yield of the compound represented by the formula (1-2) based on the compound represented by the formula (2-2) was 88%.

<Measurement of Solubility>

The solubilities in methyl isobutyl ketone at 40° C. and 60° C. of the compound represented by the formula (1-1) which was obtained in Example 2, the compound represented by the formula (1-2) which was obtained in Example 6, and the compound represented by the following formula (A)

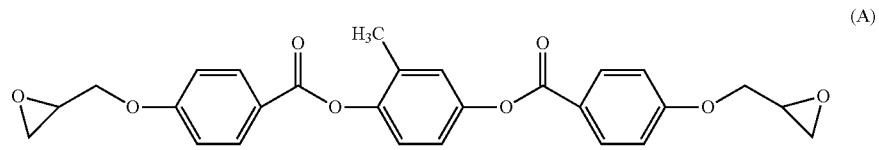 [SMILES: Cc1cc(OC(=O)c2ccc(OCC3CO3)cc2)ccc1OC(=O)c1ccc(OCC2CO2)cc1]

(compound (g)×100/[compound (g)+methyl isobutyl ketone (g)], % by weight) were measured. The results are shown in Table 1.

It is found that the solubilities of the compounds represented by the formula (1-1) and (1-2), which are the diepoxy compounds of the present invention, are more than twice as big as that of the compound represented by the formula (A) from Table 1.

TABLE 1

| | Solubility (% by weight) | |
|---|---|---|
| | 40° C. | 65° C. |
| The compound represented by the formula (1-1) | 2.36 | 4.16 |
| The compound represented by the formula (1-2) | 2.01 | 4.70 |
| The compound represented by the formula (A) | 1.10 | 2.00 |

Example 7

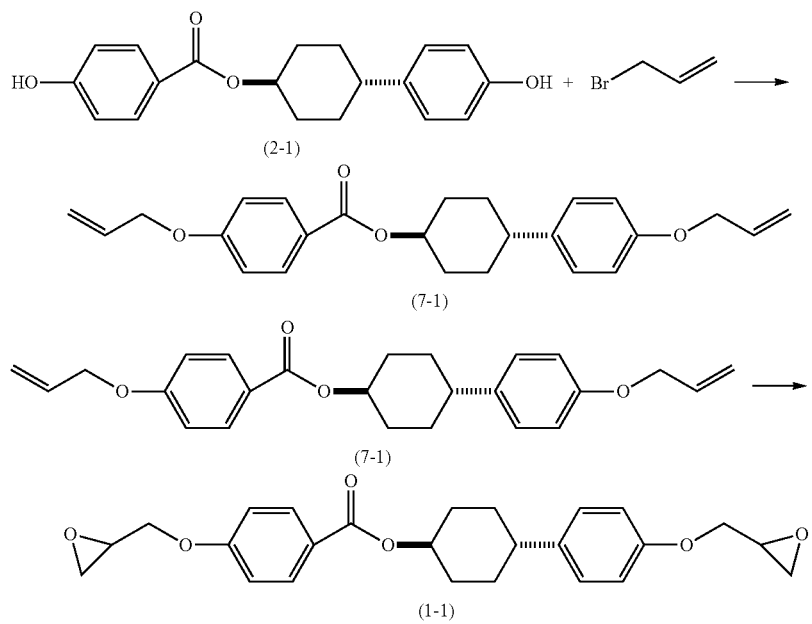

The compound represented by the above-mentioned formula (7-1) can be obtained by mixing the compound represented by the formula (2-1) which was obtained in Example 1, potassium carbonate and allyl bromide, followed by stirring the mixture obtained at a predetermined temperature.

Example 8

100 parts by weight of the compound represented by the formula (1-1), 23 parts by weight of 4,4'-diaminodiphenylmethane (manufactured by Wako Pure Chemical Industries, Ltd.) as a curing agent and N,N-dimethylformamide as a solvent were mixed to obtain a composition in a solution form.

The composition obtained was concentrated with a centrifugal concentrating apparatus to obtain a powdery composition. The powdery composition obtained was filled in an alumina pan. The alumina pan in which the composition was filled was heated with a differential scanning calorimetry apparatus (DSC Q2000 manufactured by TA Instruments) to obtain a cured product (curing condition: under an atmosphere of nitrogen, heating at 140° C. for 20 minutes, and then, heating up to 180° C. at 1° C./minute, and further heating at 200° C. for 30 minutes). The cured product obtained was cooled down to 20° C. The glass-transition temperature of the cured product was measured with a differential scanning calorimetry apparatus (heating rate: 20° C./minute), and it was 151° C.

Example 9

The composition in a solution form was obtained according to the same manner as that of Example 8 except that 19 parts by weight of 1,5-diaminonaphthalene (manufactured by Wako Pure Chemical Industries, Ltd.) was used in place of 23 parts by weight of 4,4'-diaminodiphenylmethane. The composition in a solution form obtained was concentrated with a centrifugal concentrating apparatus to obtain a powdery composition. The powdery composition obtained was heated according to the same manner as that of Example 8 to obtain a cured product. The glass-transition temperature of the cured product was 155° C.

Example 10

The composition in a solution form was obtained according to the same manner as that of Example 8 except that 36 parts by weight of cis-1,4-cyclohexene-1,2-dicarboxylic anhydride (manufactured by Tokyo Chemical Industry Co., Ltd.) was used in place of 23 parts by weight of 4,4'-diaminodiphenylmethane, and 2.7 parts by weight of 2-phenylimidazole was further added as a curing accelerator. The composition in a solution form obtained was concentrated with a centrifugal concentrating apparatus to obtain a powdery composition. The powdery composition obtained was heated according to the same manner, as that of Example 8 to obtain a cured product. The glass-transition temperature of the cured product was 145° C.

Example 11

The composition in a solution form was obtained according to the same manner as that of Example 8 except that 31 parts by weight of 5-(2,5-dioxotetrahydrofuryl)-3-methyl-3- cyclohexene-1,2-dicarboxylic anhydride (manufactured by Tokyo Chemical Industry Co., Ltd.) was used in place of 23 parts by weight of 4,4'-diaminodiphenylmethane, and 2.6 parts by weight of 2-phenylimidazole was further added as a curing accelerator. The composition in a solution form obtained was concentrated with a centrifugal concentrating apparatus to obtain a powdery composition. The powdery composition obtained was heated according to the same manner as that of Example 8 to obtain a cured product. The glass-transition temperature of the cured product was 107° C.

Example 12

The composition in a solution form was obtained according to the same manner as that of Example 8 except that 98 parts by weight of phenol novolak curing agent "MEH-7851H" (manufactured by Meiwa Plastic Industries, Ltd.) was used in place of 23 parts by weight of 4,4'-diaminodiphenylmethane, and 4.0 parts by weight of triphenylphosphine was further added as a curing accelerator. The composition in a solution form obtained was concentrated with a centrifugal concentrating apparatus to obtain a powdery composition. The powdery composition obtained was heated according to the same manner as that of Example 8 to obtain a cured product. The glass-transition temperature of the cured product was 82° C.

Example 13

The composition in a solution form was obtained according to the same manner as that of Example 8 except that 10 parts by weight of dicyandiamide (manufactured by Wako Pure Chemical Industries, Ltd.) was used in place of 23 parts by weight of 4,4'-diaminodiphenylmethane, and 2.2 parts by weight of 2-phenylimidazole was further added as a curing accelerator. The composition in a solution form obtained was concentrated with a centrifugal concentrating apparatus to obtain a powdery composition. The powdery composition obtained was heated according to the same manner as that of Example 8 to obtain a cured product. The glass-transition temperature of the cured product was 168° C.

Example 14

The composition in a solution form was prepared by mixing 100 parts by weight of the compound represented by the formula (1-1), 19 parts by weight of 1,5-diaminonaphthalene (manufactured by Wako Pure Chemical Industries, Ltd.) as a curing agent, 1094 parts by weight of an alumina powder (α-alumina powder manufactured by Sumitomo Chemical Co., Ltd.; prepared by mixing an alumina powder A1 having an average particle diameter (D50) of 18 μm, an alumina powder B1 having an average particle diameter (D50) of 3 μm and an alumina powder C1 having an average particle diameter (D50) of 0.4 μm in a weight ratio (alumina powder A1/alumina powder B1/alumina powder C1)=810/153/131 and in a volume ration (alumina powder A1/alumina powder B1/alumina powder C1)=74/14/12)), 380 parts by weight of methyl isobutyl ketone and 70 parts by weight of N,N-dimethylformamide as solvents.

The composition prepared was applied on a polyethylene terephthalate (PET) film using an applicator so that the thickness thereof became 350 μm. The PET film on which the composition was applied was dried at room temperature for 1 hour, and further dried at 140° C. for 8 minutes, followed by peeling the PET film to obtain a sheet. The sheet obtained was placed between aluminum foils having a thickness of 40 μm to conduct a vacuum press molding (press temperature: 140° C., vacuum degree: 1 kPa, press pressure: 6 MPa, treating time: 20 minutes). Then, the press temperature was increased up to 180° C. over 40 minutes. Aluminum foils were peeled to obtain a cured product in a sheet form having a thickness of 344 μm. The thermal conductivity of the cured product was measured with a xenon flash analyzer nanoflash LFA447 Type manufactured by NETZSCH, and it was 10.0 W/(m·K).

Assuming that the density of the cured product obtained by curing a composition containing the compound represented by the formula (1-1) and 1,5-diaminonaphthalene and not containing alumina powder was 1.2 g/cm$^3$ and the density of alumina powder was 3.97 g/cm$^3$, the content ratio of alumina powder in the cured product obtained was calculated. The content ratio of alumina powder in the cured product was 74% by volume.

Example 15

The composition in a solution form can be obtained by mixing 100 parts by weight of the compound represented by the formula (1-1), 19 parts by weight of 1,5-diaminonaphthalene (manufactured by Wako Pure Chemical Industries, Ltd.) as a curing agent, 380 parts by weight of methyl isobutyl ketone and 70 parts by weight of N,N-dimethylformamide as solvents. The composition obtained is impregnated into a glass fiber woven fabric having a thickness of 0.2 mm, and then, dried by heating to be able to obtain prepreg. Four sheets of the prepreg obtained are stacked and molded by press for 90 minutes under a temperature of 175° C. and a pressure of 4 MPa to be able to obtain a laminate plate.

Example 16

The composition in a solution form was prepared by mixing 100 parts by weight of the compound represented by the formula (1-2), 18 parts by weight of 1,5-diaminonaphthalene (manufactured by Wako Pure Chemical Industries, Ltd.) as a curing agent, 1089 parts by weight of an alumina powder (α-alumina powder manufactured by Sumitomo Chemical Co., Ltd.; prepared by mixing an alumina powder A1 having an average particle diameter (D50) of 18 μm, an alumina powder B1 having an average particle diameter (D50) of 3 μm and an alumina powder C1 having an average particle diameter (D50) of 0.4 μm in a weight ratio (alumina powder A1/alumina powder B1/alumina powder C1)=806/152/131 and in a volume ration (alumina powder A1/alumina powder B1/alumina powder C1)=74/14/12)), 320 parts by weight of methyl isobutyl ketone and 60 parts by weight of N,N-dimethylformamide as solvents.

The composition prepared was applied on a polyethylene terephthalate (PET) film using an applicator so that the thickness thereof became 350 μm. The PET film on which the composition was molded by press under vacuum according to the same manner as that of Example 14 to obtain a cured product in a sheet form having a thickness of 304 μm. The thermal conductivity of the cured product was measured according to the same manner as that of Example 14, and it was 9.4 W/(m·K). The content ratio of alumina powder in the cured product obtained was 74% by volume.

Example 17

The composition in a solution form was prepared by mixing 100 parts by weight of the compound represented by the formula (1-1), 19 parts by weight of 1,5-diaminonaphthalene (manufactured by Wako Pure Chemical Industries, Ltd.) as a curing agent, 579 parts by weight of an alumina powder (α-alumina powder manufactured by Sumitomo Chemical Co., Ltd.; an alumina powder having an average particle diameter (D50) of 18 μm), 210 parts by weight of methyl isobutyl ketone and 60 parts by weight of N,N-dimethylformamide as solvents.

The composition prepared was applied on a polyethylene terephthalate (PET) film using an applicator so that the thickness thereof became 350 μm. The PET film on which the composition was molded by press under vacuum according to the same manner as that of Example 14 to obtain a cured product in a sheet form having a thickness of 344 μm. The thermal conductivity of the cured product was measured according to the same manner as that of Example 14, and it was 4.7 W/(m·K).

Assuming that the density of the cured product obtained by curing a composition containing the compound represented by the formula (1-1) and 1,5-diaminonaphthalene and not containing alumina powder was 1.2 g/cm³ and the density of alumina powder was 3.97 g/cm³, the content ratio of alumina powder in the cured product obtained was calculated. The content ratio of alumina powder in the cured product was 60% by volume.

INDUSTRIAL APPLICABILITY

The diepoxy compound of the present invention has a superior solubility in methyl isobutyl ketone. The cured product obtained by curing the composition containing the diepoxy compound has a high thermal conductivity.

The invention claimed is:

1. A diepoxy compound represented by the formula (1)

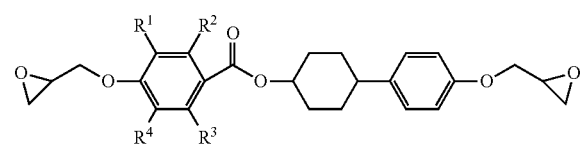

(1)

wherein $R^1$, $R^2$, $R^3$ and $R^4$ independently each represent a hydrogen atom or an alkyl group having 1 to 3 carbon atoms.

2. The diepoxy compound according to claim 1, wherein the compound represented by the formula (1) is a compound represented by the formula (1')

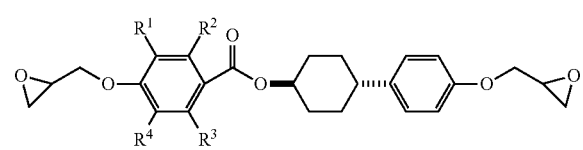

(1')

wherein $R^1$, $R^2$, $R^3$ and $R^4$ are the same meaning as defined above.

3. A process for producing a diepoxy compound represented by the formula (1)

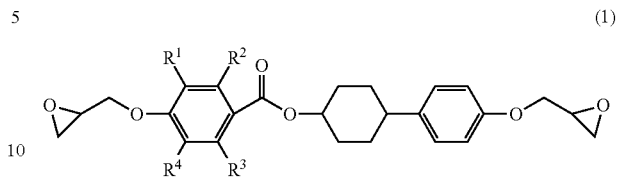

(1)

wherein $R^1$, $R^2$, $R^3$ and $R^4$ independently each represent a hydrogen atom or an alkyl group having 1 to 3 carbon atoms, comprising reacting a dihydroxy compound represented by the formula (2)

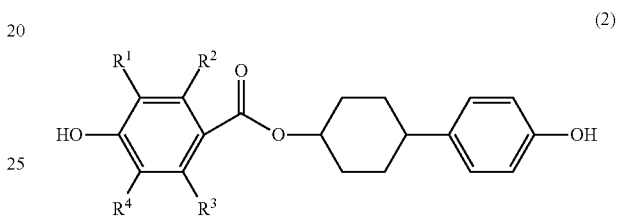

(2)

wherein $R^1$, $R^2$, $R^3$ and $R^4$ are the same meaning as defined above, with an epihalohydrin represented by the formula (3)

(3)

wherein $X^1$ represents a halogen atom, in the presence of an ammonium salt and an inorganic base.

4. The process according to claim 3, wherein the reaction is conducted by mixing the dihydroxy compound represented by the formula (2) with the epihalohydrin represented by the formula (3) and the ammonium salt, and the reaction is further conducted by mixing the mixture obtained with the inorganic base.

5. The process according to claim 3, wherein the inorganic base is sodium hydroxide or potassium hydroxide.

6. A dihydroxy compound represented by the formula (2)

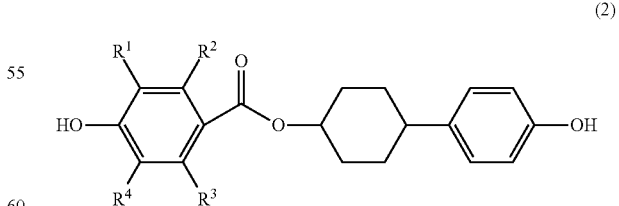

(2)

wherein $R^1$, $R^2$, $R^3$ and $R^4$ independently each represent a hydrogen atom or an alkyl group having 1 to 3 carbon atoms.

7. The dihydroxy compound according to claim 6, wherein the compound represented by the formula (2) is a compound represented by the formula (2')

(2')

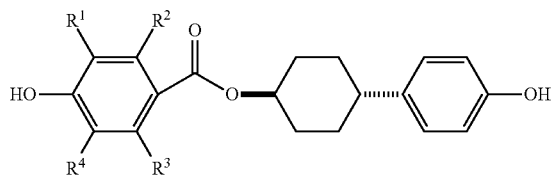

wherein $R^1$, $R^2$, $R^3$ and $R^4$ independently each represent a hydrogen atom or an alkyl group having 1 to 3 carbon atoms.

8. A process for producing a dihydroxy compound represented by the formula (2)

(2)

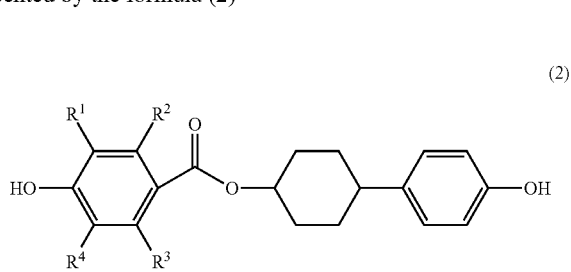

wherein $R^1$, $R^2$, $R^3$ and $R^4$ independently each represent a hydrogen atom or an alkyl group having 1 to 3 carbon atoms, comprising reacting a compound represented by the formula (5)

(5)

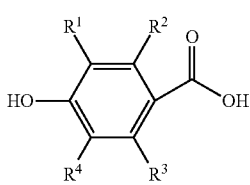

wherein $R^1$, $R^2$, $R^3$ and $R^4$ are the same meaning as defined above, with a compound represented by the formula (6)

(6)

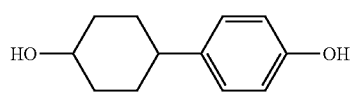

in the presence of an acid.

9. A composition containing a diepoxy compound represented by the formula (1)

(1)

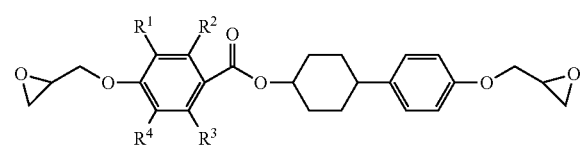

wherein $R^1$, $R^2$, $R^3$ and $R^4$ independently each represent a hydrogen atom or an alkyl group having 1 to 3 carbon atoms, and a curing agent.

10. The composition according to claim 9, wherein the curing agent is at least one curing agent selected from the group consisting of an amine curing agent, a phenol curing agent and an acid anhydride curing agent.

11. The composition according to claim 10, wherein the amine curing agent is at least one selected from the group consisting of 4,4'-diaminodiphenylmethane, 4,4'-diaminodiphenylethane, 1,5-diaminonaphthalene and p-phenylenediamine.

12. A cured product obtained by curing the composition according to claim 9.

13. A prepreg obtained by coating on a base material or impregnating a base material with the composition according to claim 9, followed by semi-curing.

14. A composition containing a diepoxy compound represented by the formula (1)

(1)

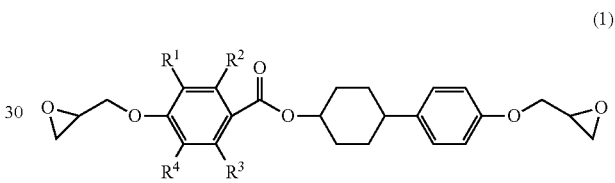

wherein $R^1$, $R^2$, $R^3$ and $R^4$ independently each represent a hydrogen atom or an alkyl group having 1 to 3 carbon atoms, a curing agent and alumina.

15. The composition according to claim 14, which contains 75 to 95 parts by weight of alumina relative to 100 parts by weight of sum of the diepoxy compound represented by the formula (1) and the curing agent.

16. The composition according to claim 14, wherein the alumina is a mixture of a component A having D50 (a particle size at 50% cumulative volume) of 2 m or more and 100 m or less, a component B having D50 of 1 m or more and 10 m or less, and a component C having D50 of 0.01 m or more and 5 m or less, and the content of the component A, that of the component B and that of the component C are respectively 50 to 90% by volume, 5 to 40% by volume, and 1 to 30% by volume, relative to 100% by volume of sum of the component A, the component B and the component C.

17. A cured product obtained by curing the composition according to claim 14.

18. The cured product according to claim 17, wherein the content of alumina contained in the cured product is 50 to 80% by volume.

* * * * *